United States Patent
Cragg et al.

(10) Patent No.: US 7,048,710 B1
(45) Date of Patent: May 23, 2006

(54) SYSTEM AND METHOD FOR FACILITATING HEMOSTASIS OF BLOOD VESSEL PUNCTURES WITH ABSORBABLE SPONGE

(75) Inventors: Andrew H. Cragg, Edina, MN (US); Rodney Brenneman, San Juan Capistrano, CA (US); Mark Ashby, Laguna Niguel, CA (US)

(73) Assignee: Sub-Q, Inc., San Clemente, CA (US)

(*) Notice: Subject to any disclaimer, the term of this patent is extended or adjusted under 35 U.S.C. 154(b) by 166 days.

(21) Appl. No.: 09/613,439

(22) Filed: Jul. 11, 2000

Related U.S. Application Data

(62) Division of application No. 09/071,284, filed on May 1, 1998, now Pat. No. 6,162,192.

(51) Int. Cl.
*A61F 13/20* (2006.01)

(52) U.S. Cl. ............................ 604/15; 604/60

(58) Field of Classification Search ............ 604/11–18, 604/57–60, 93, 158, 164, 264, 286, 93.01, 604/266; 606/191, 213–216, 151
See application file for complete search history.

(56) References Cited

U.S. PATENT DOCUMENTS

| | | | |
|---|---|---|---|
| 581,235 A | 4/1897 | Kenyon |
| 1,578,517 A | 3/1926 | Hein |
| 2,086,580 A | 7/1937 | Shirley |
| 2,370,319 A | 2/1945 | Lippincott |
| 2,465,357 A | 3/1949 | Correll |
| 2,492,458 A | 12/1949 | Bering, Jr. |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,874,776 A | 2/1959 | Hooe |

(Continued)

FOREIGN PATENT DOCUMENTS

EP 32826 A2 7/1981

(Continued)

OTHER PUBLICATIONS

Vincent P. Chuang, M.D., et al., "Sheath Needle for Liver Biopsy in High-Risk Patients", *Radiology*, 166:261-262 (1988).

(Continued)

*Primary Examiner*—Michele Kidwell
(74) *Attorney, Agent, or Firm*—Miller, Matthias & Hull

(57) ABSTRACT

A system for facilitating hemostasis of a puncture site in a blood vessel injects an absorbable sponge pledget in a hydrated state at an exterior of the blood vessel puncture to facilitate hemostasis. The system includes a tract dilator for locating the puncture, an introducer, and a plunger. The introducer includes a staging chamber for receiving the absorbent sponge pledget and a delivery chamber having a diameter smaller than a diameter of the staging chamber into which a hydrated pledget passes. The pledget is hydrated and compressed within the introducer and then ejected with the plunger to the delivery site to facilitate hemostasis of the blood vessel puncture. The system delivers the absorbable sponge pledget over a guidewire to ensure the proper positioning of the pledget over the puncture. The implanted absorbable sponge once delivered expands rapidly to fill the target site and is absorbed by the body over time.

36 Claims, 5 Drawing Sheets

U.S. PATENT DOCUMENTS

| | | |
|---|---|---|
| 2,899,362 A | 8/1959 | Sieger, Jr. et al. |
| 2,997,195 A | 8/1961 | Chuen Yuen |
| 3,157,524 A | 11/1964 | Artandi |
| 3,358,689 A | 12/1967 | Higgins |
| 3,411,505 A | 11/1968 | Nobis |
| 3,703,174 A | 11/1972 | Smith |
| 3,724,465 A | 4/1973 | Duchane |
| 3,736,939 A | 6/1973 | Taylor |
| 4,000,741 A | 1/1977 | Binard et al. |
| 4,098,728 A | 7/1978 | Rosenblatt |
| 4,211,323 A | 7/1980 | Olsen ..................... 206/210 |
| 4,218,155 A | 8/1980 | Weidner .................. 401/132 |
| 4,219,026 A | 8/1980 | Layton |
| 4,224,945 A | 9/1980 | Cohen |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zulowski |
| 4,404,970 A | 9/1983 | Sawyer |
| 4,405,314 A | 9/1983 | Cope |
| 4,515,637 A | 5/1985 | Cioca |
| 4,573,573 A | 3/1986 | Favaro |
| 4,573,576 A | 3/1986 | Krol |
| 4,587,969 A | 5/1986 | Gillis |
| 4,588,395 A | 5/1986 | Lemelson |
| 4,591,094 A | 5/1986 | Morris |
| 4,619,261 A | 10/1986 | Guerrero |
| 4,619,913 A | 10/1986 | Luck et al. |
| 4,644,649 A | 2/1987 | Seaman et al. |
| 4,645,488 A | 2/1987 | Matukas |
| 4,699,616 A | 10/1987 | Norwak |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,832,688 A | 5/1989 | Sagae et al. |
| 4,836,204 A | 6/1989 | Landymore et al. |
| 4,839,204 A | 6/1989 | Yoshino |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,106,376 A | 4/1992 | Monenen et al. |
| 5,108,421 A | 4/1992 | Fowler |
| 5,129,889 A | 7/1992 | Hahn |
| 5,160,323 A | 11/1992 | Andrew |
| 5,163,904 A | 11/1992 | Lampropoulous et al. |
| 5,167,624 A | 12/1992 | Butler et al. |
| 5,192,290 A | 3/1993 | Hilgal |
| 5,192,300 A | 3/1993 | Fowler |
| 5,192,301 A | 3/1993 | Kamiya et al. |
| 5,195,988 A | 3/1993 | Haaga |
| 5,219,899 A | 6/1993 | Panster et al. |
| 5,220,926 A | 6/1993 | Jones |
| 5,221,259 A | 6/1993 | Weldon et al. |
| 5,222,974 A | 6/1993 | Kensey et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,292,309 A | 3/1994 | Van Tassel et al. |
| 5,299,581 A | 4/1994 | Donnell et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammerslag |
| 5,385,550 A | 1/1995 | Su et al. |
| 5,388,588 A | 2/1995 | Nabai et al. |
| 5,391,183 A | 2/1995 | Janzen et al. |
| 5,395,353 A | 3/1995 | Scribner |
| 5,399,361 A | 3/1995 | Song et al. |
| 5,417,699 A | 5/1995 | Klein et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kenesey et al. |
| 5,447,502 A | 9/1995 | Haaga |
| 5,458,570 A | 10/1995 | May, Jr. |
| 5,462,194 A | 10/1995 | Barawell |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers et al. |
| 5,490,736 A | 2/1996 | Haber et al. .................. 401/40 |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,529,577 A | 6/1996 | Hammerslag |
| 5,540,715 A | 7/1996 | Katsaros et al. |
| 5,542,914 A | 8/1996 | Van Iten |
| 5,545,175 A | 8/1996 | Abidin et al. |
| 5,545,178 A | 8/1996 | Kensey et al. |
| 5,554,108 A | 9/1996 | Browning et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,207 A | 2/1997 | Paczonay |
| 5,601,601 A | 2/1997 | Tal et al. |
| 5,601,602 A | 2/1997 | Fowler |
| 5,601,603 A | 2/1997 | Illi |
| 5,620,461 A | 4/1997 | Muijs Van De Moer |
| 5,624,685 A | 4/1997 | Takahashi et al. |
| 5,645,566 A | 7/1997 | Brenneman et al. |
| 5,645,849 A | 7/1997 | Pruss et al. |
| 5,649,547 A | 7/1997 | Ritchart et al. |
| 5,653,730 A | 8/1997 | Hammerslag |
| 5,665,107 A | 9/1997 | Hammerslag |
| 5,674,346 A | 10/1997 | Kundel |
| 5,676,689 A | 10/1997 | Kensey et al. |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,827,218 A | 10/1998 | Nguyen et al. |
| 5,830,130 A | 11/1998 | Janzen et al. |

| | | |
|---|---|---|
| 5,858,008 A | 1/1999 | Capaccio |
| 5,861,004 A | 1/1999 | Kensey et al. |
| 5,868,762 A | 2/1999 | Cragg et al. |
| 5,902,310 A | 5/1999 | Foerster et al. |
| 5,931,165 A | 8/1999 | Reich et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,033,427 A | 3/2000 | Lee |
| 6,056,768 A | 5/2000 | Cates et al. |
| 6,063,061 A | 5/2000 | Wallace et al. |
| 6,063,085 A | 5/2000 | Tay et al. |
| 6,066,325 A | 5/2000 | Wallace et al. |
| 6,071,300 A | 6/2000 | Brenneman et al. |
| 6,071,301 A | 6/2000 | Cragg et al. |
| 6,086,607 A | 7/2000 | Cragg et al. |
| 6,090,130 A | 7/2000 | Nash et al. |
| 6,126,675 A | 10/2000 | Shchervinsky et al. |
| 6,161,034 A | 12/2000 | Burbank et al. |
| 6,162,192 A | 12/2000 | Cragg et al. |
| 6,183,497 B1 | 2/2001 | Sing et al. |
| 6,197,327 B1 | 3/2001 | Harrison et al. |
| 6,200,328 B1 | 3/2001 | Cragg et al. |
| 6,315,753 B1 | 11/2001 | Cragg |
| 6,325,789 B1 | 12/2001 | Janzen et al. |
| 6,371,974 B1 | 4/2002 | Brenneman et al. |
| 6,440,151 B1 | 8/2002 | Cragg et al. |
| 6,440,153 B1 | 8/2002 | Cragg et al. |
| 6,447,534 B1 | 9/2002 | Cragg et al. |
| 6,503,222 B1 | 1/2003 | Lo |
| 6,527,734 B1 | 3/2003 | Cragg et al. |
| 6,540,735 B1 | 4/2003 | Ashby et al. |
| 6,544,236 B1 | 4/2003 | Cragg et al. |
| 6,547,806 B1 | 4/2003 | Ding |
| 6,585,680 B1 | 7/2003 | Bugge |
| 6,610,026 B1 | 8/2003 | Cragg et al. |
| 2002/0002889 A1 | 1/2002 | Ashby et al. |
| 2002/0016612 A1 | 2/2002 | Ashby et al. |
| 2002/0038133 A1 | 3/2002 | Sing et al. |
| 2002/0042378 A1 | 4/2002 | Reich et al. |
| 2002/0062104 A1 | 5/2002 | Ashby et al. |
| 2002/0156495 A1 | 10/2002 | Brenneman et al. |
| 2003/0028140 A1 | 2/2003 | Greff et al. |
| 2003/0088269 A1 | 5/2003 | Ashby |
| 2003/0088271 A1 | 5/2003 | Cragg et al. |
| 2003/0120258 A1 | 6/2003 | Ashby et al. |
| 2003/0135237 A1 | 7/2003 | Cragg et al. |
| 2004/0019328 A1 | 1/2004 | Sing et al. |
| 2004/0019330 A1 | 1/2004 | Ashby |

FOREIGN PATENT DOCUMENTS

| | | | |
|---|---|---|---|
| EP | 476178 | 3/1992 | ................... 17/12 |
| EP | 482350 A2 | 4/1992 | |
| EP | 0557963 | 2/1993 | |
| EP | 0637432 B1 | 9/1994 | |
| EP | 0637431 | 11/1994 | |
| FR | 2641692 | 1/1990 | |
| GB | 1509023 | 4/1978 | |
| GB | 1569660 | 6/1980 | |
| RU | 782814 | 11/1980 | |
| RU | 1088709 A | 4/1984 | |
| WO | WO 91/12847 | 9/1991 | |
| WO | WO 94/02072 | 3/1994 | |
| WO | WO 94/28800 | 12/1994 | |
| WO | WO 95/28124 | 10/1995 | |
| WO | WO 95/32669 | 12/1995 | |
| WO | WO 95/32671 | 12/1995 | |
| WO | WO 95/32679 | 12/1995 | |
| WO | WO 96/08208 | 3/1996 | |
| WO | WO 96/24290 | 8/1996 | |
| WO | WO 97/07934 | 3/1997 | |
| WO | WO 98/06346 | 2/1998 | |
| WO | WO 99/66834 | 12/1999 | |
| WO | WO 04/93649 | 11/2004 | |

OTHER PUBLICATIONS

Marc Zins, M.D., et al., "US-guided Percutaneous Liver Biopsy with Plugging of the Needle Track: A Prospective Study in 72 High-Risk Patients", *Radiology*, 184(3):841-843 (1992).

Tony P. Smith, M.D., et al., "Percutaneous Transhepatic Liver Biopsy with Tract Embolization", *Radiology*, 198:769-774 (1996).

S.A. Riley, et al., "Percutaneous Liver Biopsy with Plugging of Needle Track: A Safe Method for Use in Patients with Impaired Coagulation", *The Lancet*, p. 436 (1984).

David J. Allison, M.D., et al., "Percutaneous Liver Biopsy and Track Embolization with Steel Coils", *Radiology*, 169(1):261-263 (1988).

Sigmund Silber, M.D., FACC, "Rapid Hemostasis of Arterial Puncture Sites with Collagen in Patients Undergoing Diagnostic and Interventional Cardiac Catheterization", *Clinical Cardiology*, 20:981-992 (1997).

Ferdinand Kiemeneij, MD, et al., "Improved Anticoagulation Management After Palmaz Schatz Coronary Stent Implantation by Sealing the Arterial Puncture Site With a Vascular Hemostasis Device", *Catheterization and Cardiovascular Diagnosis*, 30:317-322 (1993).

J.P.M. Foran, et al., "*Early Mobilisation After Percutaneous Cardiac Catheterisation Using Collagen Plug (VasoSeal) Haemostasis*," Br Heart, vol. 69 (1993) pp. 424-429.

Schrader, R., "*Collagen Application*," Catheterization and Cardiovascular Diagnosis, (1992) pp. 298-302.

JSR Gibbs, "*Fermoral Arterial Hemostasis*," Journal of Interventional Cardiology, v 5 (1992) pp 85-88.

W.G. Kussmaul, "*Rapid Arterial Hemostasis*," Journal of the American College of Cardiology, vol. 25 (1995) pp. 1685-1692.

Timothy A. Sanborn, MD, et al., "*Multicenter Randomized Trial Comparing a Percutaneous Collagen Hemostasis Device With Conventional Manual Compression After Diagnostic Angiography and Angioplasty*," Journal of American College of Cardiology, vol. 22, No. 5 (1993) pp. 1273-1279.

Pharmacia & Upjohn Manufacturer Brochure "*Gelfoam Sterile Sponge, Sterile Powder, and Sterile Film*," (May 1997): pp. 1-34.

Pharmacia & Upjohn Manufacturer Brochure, "*Gelfoam Sterile Powder*," (Mar. 1996).

Pharmacia & Upjohn Manufacturer Specification "*Gelfoam Sterile Sponge, Sterile Powder, and Sterile Film*," (Nov. 1996): pp. 1-23.

Pharmacia & Upjohn Manufacturer Brochure for Gelfoam, 1996.

Pharmacia & Upjohn Manufacturer, "Gelfoam Sterile Powder," (Feb. 1996).

Ashby, Mark et al; U.S. Appl. No. 10/287,922; filed Nov. 4, 2002; entitled: Apparatus And Method For Inhibiting Blood Loss.

Ashby, Mark et al; U.S. Appl. No. 10/069,107; filed Dec. 16, 2002; entitled: Device And Method For Determining A Depth Of An Incision.

Ashby, Mark et al; U.S. Appl. No. 10/278,710; filed Oct. 22, 2002; entitled: System and Method for Facilitating Hemostasis of Blood Vessel Punctures With Absorbable Sponge.

Ashby, Mark et al; U.S. Appl. No. 10/334,770, filed Dec. 31, 2002; entitled: Improved System and Method for Facilitating Hemostasis with Absorbable Sponge.

Ashby, Mark et al; U.S. Appl. No. 10/421,680; filed Apr. 22, 2003; entitled: Puncture Closure System With Pin And Pull Technique.

Ashby, Mark et al; U.S. Appl. No. 10/462,065; filed Jun. 12, 2003; entitled: Enhanced Bleed Back System.

Ashby, Mark et al, U.S. Appl. No. 10/462,064; filed Jun. 12, 2003; entitled: Release Mechanism.

Ashby, Mark et al; U.S. Appl. No. 10/461,587; filed Jun. 12, 2003; entitled: Dissolvable Closure Device.

Ashby, Mark et al; U.S. Appl. No. 10/461,035; filed Jun. 13, 2003; entitled: System And Method For Delivering Hemostasis Promoting Material To A Blood Vessel Puncture Site.

Ashby, Mark et al; U.S. Appl. No. 10/461,006; filed Jun. 13, 2003; entitled: System and Method for Delivering Hemostasis Promoting Material to a Blood Vessel Puncture with a Staging Tube.

Ashby, Mark et al; U.S. Appl. No. 10/460,859; filed Jun. 12, 2003; entitled: Hemostatic Device Including a Capsule.

Ashby, Mark et al; U.S. Appl. No. 10/732,441; filed Dec. 9, 2003; entitled: Pledget-Handling System and Method for Delivering Hemostasis Promoting Material to a Blood Vessel Puncture Site By Fluid Pressure.

Ashby, Mark et al; U.S. Appl. No. 10/754,824; filed Jan. 9, 2004; entitled: Sheath-Mounted Arterial Plug Delivery Device.

Berman, et al "Guided Direct Antegrade Puncture of the Superficial Femoral Artery" AJR 147:632-634, Sep. 1986 0361-803X/86/1473-0632 © American Roentgen Ray Society.

Berman et al "Modification of the Cope Drainage Catheter to Facilitate Placement" AJR 146:169-170, Jan. 1986 0361-803X/86/1461-0169 © American Ray Society.

Bryne, J. Review, Article: Endovascular treatments for intracranial aneurysms, 1996 The British Journal of radiology; 98,891-899.

Correll, John T. et al. Biologic investigations of new absorbable sponge; p. 585.

Correll, John T., al., Certain Properties of a New Physiologically Absorbable Sponge pp-233-235, 14908.P.

Fandrich, C., t al "Small guage gelfoam plug liver biopsy in high risk patients", Australian Radiology, vol. 40, pp. 230-234 (1996).

Kassell, et al. Size of Intracanial aneurysm; vol. 12, No. 3, (1983).

Saddekni, MD et al "Antegrade Catheterization of the Superficial Femoral Artery" Radiology 1985 157:561-532.

Szikora, et al. "Combined Use of Stents and cells to treat experimental wide-necked carotid anueryms"; Preliminary results; AJNR AM newradiol 15: 1091-1102, Jun. 1994.

Szikora, et al. Endovascular treatment of experimental annuerysms with liquid polymers: vol. 38, No. 2, Feb. 1996.

Turjman, et al. "Combined Stent implantation & endosacular coil placement for treatment of experimental wide-necked aneurysms": AJNRAM J. Neuroradio 15: 1087-1090 Jun. 1994.

Vogelzang "A Modified Cope Introducing Dilator to Allow Straight Guide Wire Introduction" AJR 146:381-382 Feb. 1986 0361-803X/86/1462-0381 © American Roentgen Ray Society.

Yoshimoto, et al "Cerebral aneurysms unrelated to arterial bifurcations"; Acta neurochir (Wien) (96) 138: 958-964.

Pharmacia & Upjohn manufacturer brochure, "gelfoam sterile powder" (Sep. 1996).

(34298-203) Ashby et al; U.S. Appl. No. 10/978,321; filed Oct. 29, 2004; entitled: "Absorbable Sponge With Contrasting Agent".

(34298-204) Ashby et al; U.S. Appl. No. 10/959,898; filed Dec. 5, 2004; entitled: "Method For Sterilizing Cross-Linked Gelatin Compositions".

Di Seni, Ricardo, Part 1, Embolotherapy: Agents, Equipment, and Techniques, *Vascular Embolotherapy*, vol. 4, p. 29.

Scheiveink, "Intracanial Aneursysms", The New *England Journal of Medicine; Review Articles*, Jan. 2, 1997.

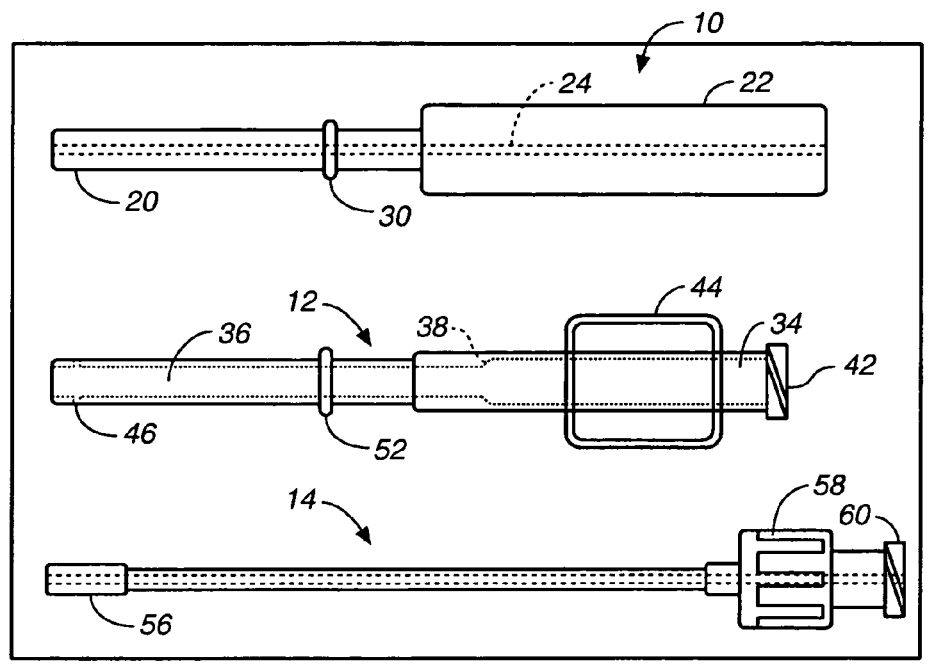
FIG._1
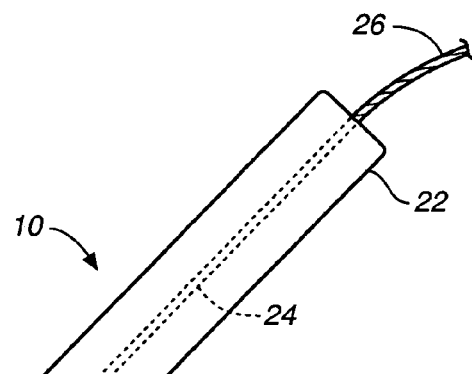
FIG._2

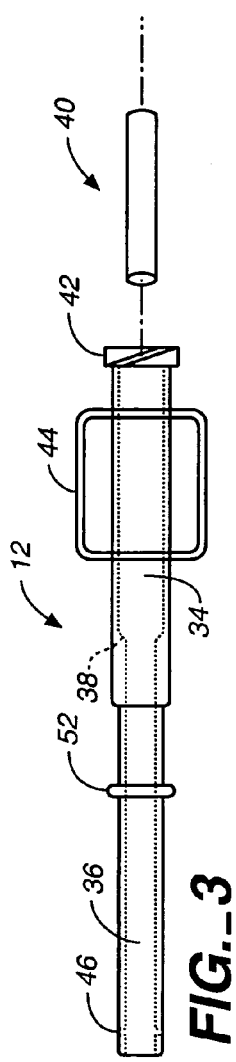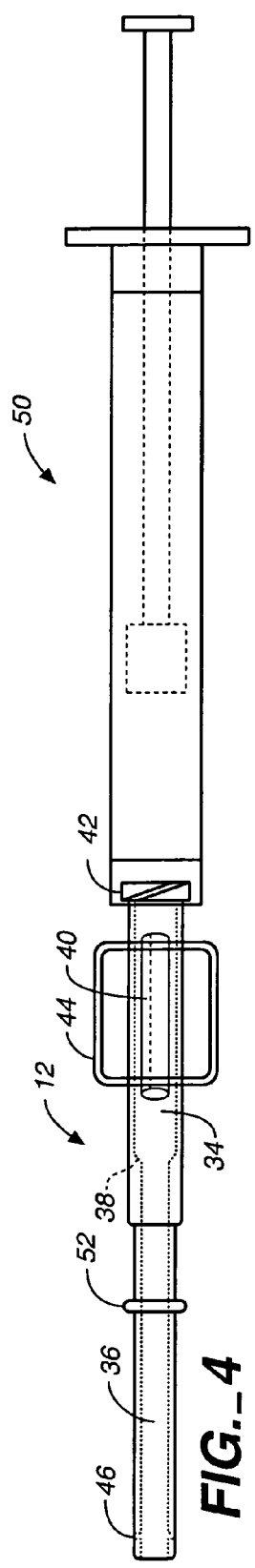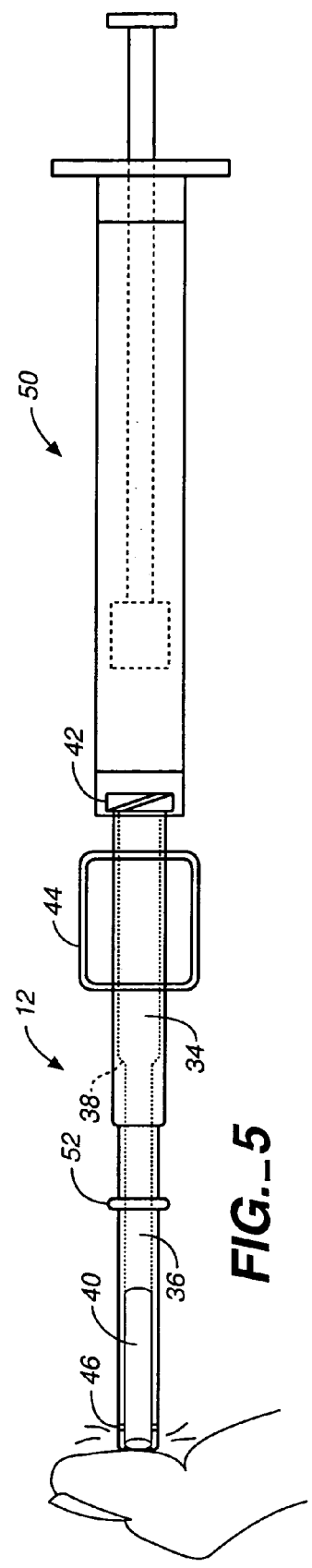

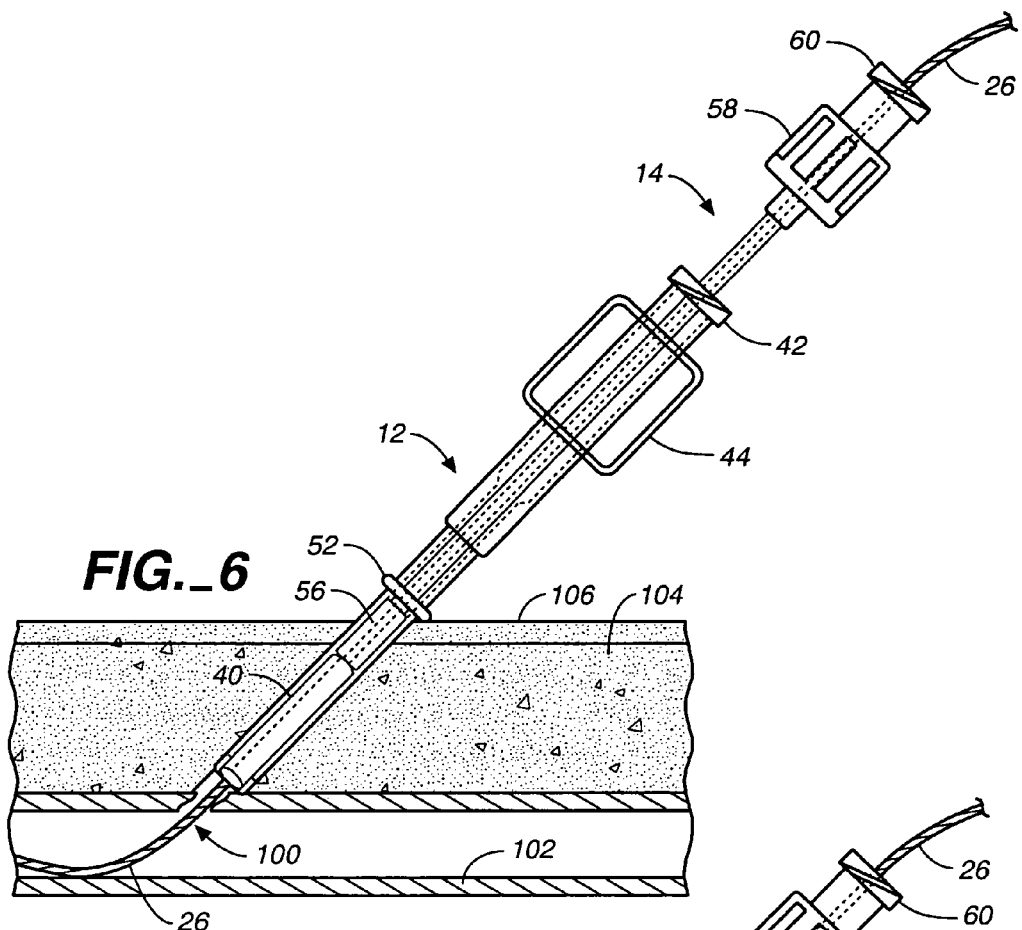
FIG._6
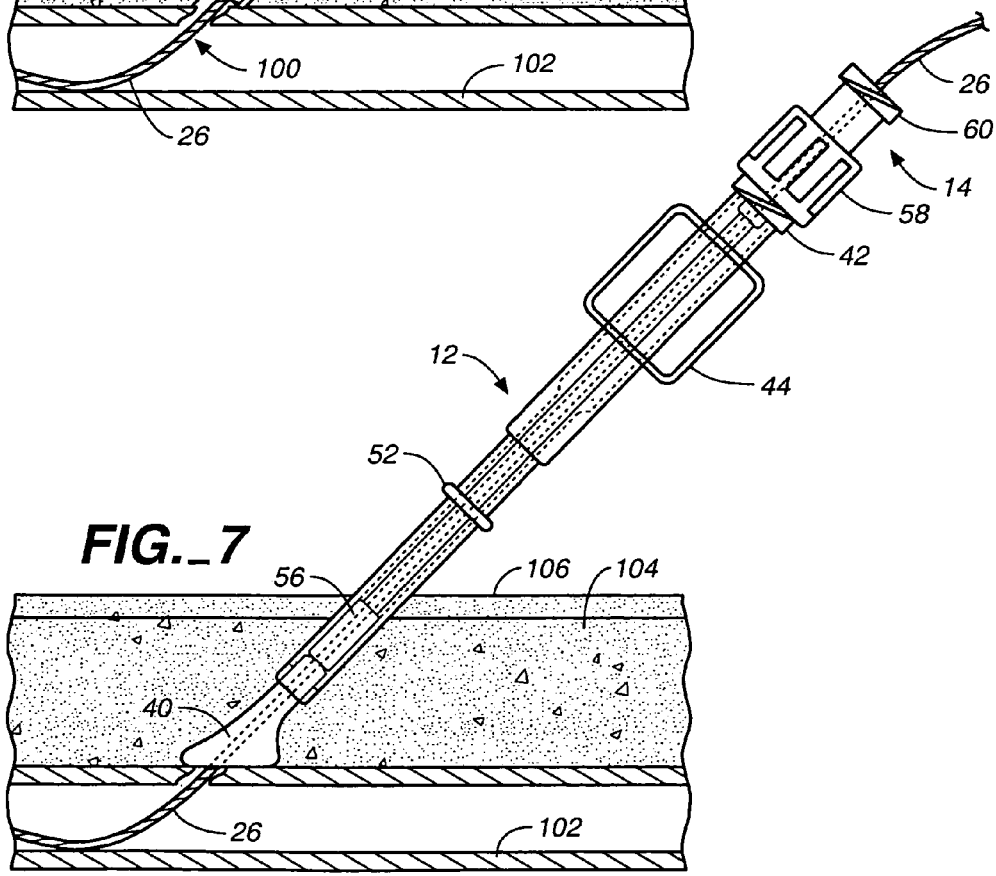
FIG._7

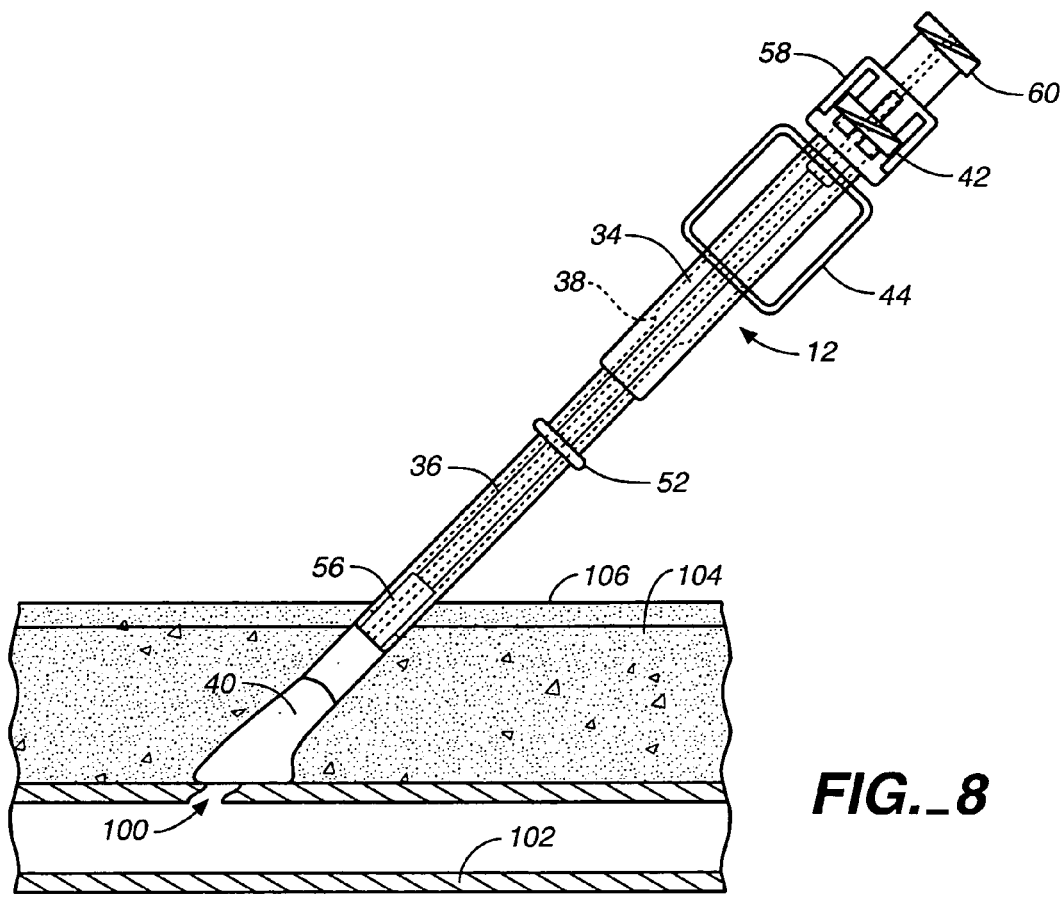
FIG._8
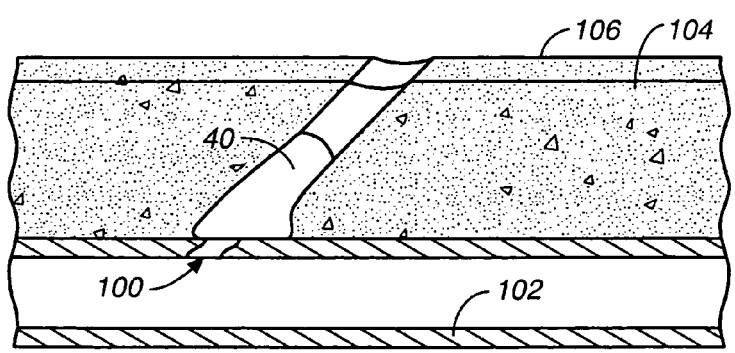
FIG._9

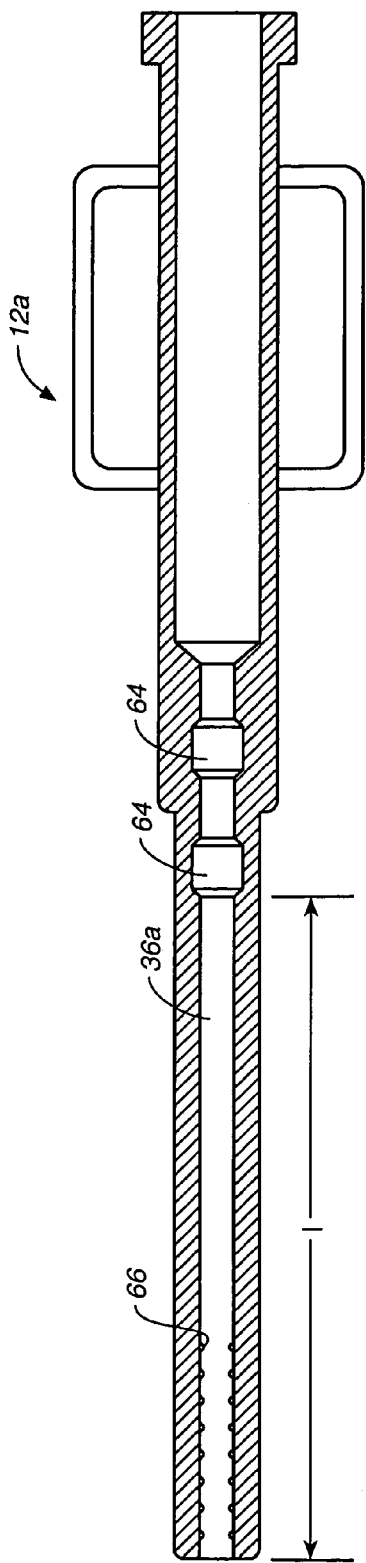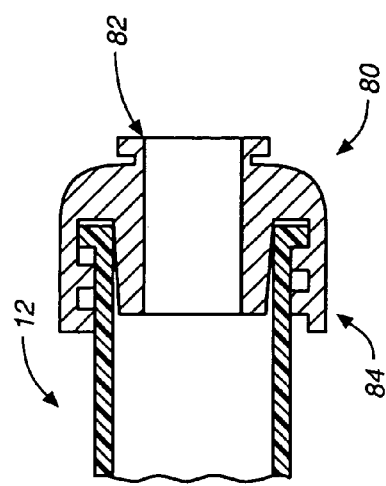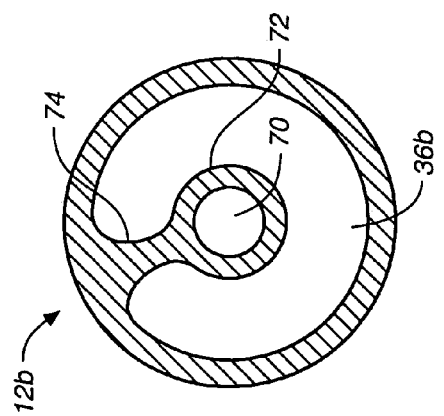

SYSTEM AND METHOD FOR FACILITATING HEMOSTASIS OF BLOOD VESSEL PUNCTURES WITH ABSORBABLE SPONGE

This application is a divisional, of application Ser. No. 09/071,284, filed May 1, 1998 now U.S. Pat. No. 6,162,192.

BACKGROUND OF THE INVENTION

1. Field of the Invention

The invention relates to a closure system for blood vessel punctures, and more particularly, the invention relates to a system and method for facilitating hemostasis of blood vessel punctures with an absorbable sponge material.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for a up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Yet another approach to subcutaneous puncture closure involves the internal suturing of the blood vessel puncture with a specially designed suturing device. However, these suturing devices involve a significant number of steps to perform suturing and require substantial expertise.

Accordingly, it would be desirable to provide a system for facilitating hemostasis of blood vessel punctures which addresses the drawbacks of the known systems.

SUMMARY OF THE INVENTION

One aspect of the present invention relates to a device for facilitating hemostasis of a puncture in the wall of a blood vessel including an introducer for hydrating and compressing an absorbable sponge pledget for delivery to a patient to facilitate hemostasis of the puncture and a plunger insertable into the introducer for ejection of the pledget from the introducer into a patient to seal the puncture in the blood vessel wall. The introducer includes a staging chamber with a first diameter configured to receive the absorbable sponge pledget, a delivery chamber with a second diameter smaller than the first diameter, and a tapered section between the staging chamber and the delivery chamber for compressing the pledget.

In accordance with another aspect of the present invention, a system for facilitating hemostasis of a puncture in the wall of a blood vessel includes a tract dilator, an introducer, and a plunger each having a lumen for allowing the tract dilator, introducer, and plunger to be passed over a guidewire. The introducer lumen includes a staging chamber configured to receive an absorbable sponge pledget and a delivery chamber. The plunger is insertable into the introducer for ejection of the pledget from the delivery chamber into a patient to facilitate hemostasis of a puncture in a blood vessel wall.

In accordance with an additional aspect of the present invention, a method for facilitating hemostasis of a puncture in the wall of a blood vessel includes the steps of: establishing a depth of a blood vessel puncture from the skin of a patient; loading an introducer with an absorbable sponge pledget by hydrating and compressing the pledget; loading the introducer over a guidewire positioned in the blood vessel by inserting the guidewire through the hydrated and compressed pledget; and ejecting the pledget adjacent the blood vessel puncture to facilitate hemostasis of the puncture while maintaining the guidewire in place.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a top view of a blood vessel puncture sealing kit;

FIG. 2 is a side cross sectional view of a punctured blood vessel and a tract dilator for locating the puncture;

FIG. 3 is a side view of an introducer and pledget prior to placement within the introducer;

FIG. 4 is a side view of an introducer having a pledget positioned within the introducer staging chamber and a syringe attached to the introducer;

FIG. 5 is a side view of the introducer and syringe with the pledget hydrated and advanced to a delivery chamber within the introducer;

FIG. 6 is a side cross sectional view of a punctured blood vessel with the introducer and plunger positioned for delivery of the pledget;

FIG. 7 is a side cross sectional view of a punctured blood vessel with the pledget being deposited at the puncture site;

FIG. 8 is a side cross sectional view of a punctured blood vessel with a hydrated and kneaded pledget deposited at the puncture site, the guidewire removed, and the delivery system being withdrawn;

FIG. 9 is a side cross sectional view of a punctured blood vessel with a hydrated and kneaded pledget facilitating hemostasis of the puncture site;

FIG. 10 is a side cross sectional view of an alternative embodiment of an introducer;

FIG. 11 is a cross sectional view of a distal end of an introducer according to another alternative embodiment having a central channel for receiving the guidewire; and FIG. 12 is a cross sectional side view of a distal end of an introducer with a connector for connecting a syringe.

DETAILED DESCRIPTION OF THE PREFERRED EMBODIMENTS

An over the wire delivery system delivers an absorbable sponge pledget in a hydrated condition to a blood vessel puncture site to achieve hemostasis. The over the wire delivery system includes a tract dilator 10, an introducer 12, and a pusher 14, illustrated in kit form in FIG. 1. The system allows over the wire delivery of the absorbable sponge material directly to the puncture site to achieve hemostasis. Over the wire delivery ensures that the sponge material is properly positioned to fully occlude the puncture. In addition, the absorbable sponge material is delivered in a hydrated state which immediately expands to stop blood flow through the puncture. The introducer allows the delivery of more absorbable sponge material through a smaller tract by hydrating and compressing the absorbable sponge material.

Prior to discussing the present invention in further detail, the following terms are defined:

"Pledget" means a piece of absorbable sponge formed into a generally elongated shape having a size which allows delivery in a hydrated state through a delivery cannula, or introducer to a site of a puncture in a blood vessel.

"Absorbable sponge" means a biocompatible material which is capable of being hydrated, is resiliently compressible in a hydrated state, and when implanted within a human or other mammalian body is absorbed by the body. Preferably the absorbable sponge is non-immunogenic.

"Hydrate" means to partially or fully saturate with a fluid, such as, saline, water, contrast agent, thrombin, therapeutic agents, or the like.

"Kneading" of the absorbable sponge material means both dry and wet manipulation of sponge material which compresses, enlarges, or changes the shape of the sponge material causing the sponge material to have improved expansion response.

As shown in FIG. 1, the tract dilator 10, the introducer 12, and the pusher 14 may be provided to a medical facility in the form of a kit or individually. The tract dilator 10 as illustrated in FIGS. 1 and 2 includes a distal tip 20, a proximal end 22, and a lumen 24 extending from the distal tip to the proximal end of the tract dilator. The lumen 24 is provided to allow the tract dilator 10 to be received over a guidewire 26 which extends through the puncture wound 100 into the blood vessel 102. The tract dilator 10 may have a constant cross section or may taper slightly to a smaller diameter at the distal tip 20. According to an alternative embodiment, the tract dilator 10 may have a narrow shaft with an enlarged distal tip. The distal tip 20 has rounded edges to prevent catching on subcutaneous tissue 104 as the tract dilator 10 is inserted through the skin 106 and tissue to the blood vessel puncture site. The tract dilator distal tip 20 has a diameter such that the tip of the tract dilator will not pass into the blood vessel but will stop and provide tactile feedback when it reaches the external blood vessel wall 102.

A depth indicator 30 is positioned around the tract dilator 10 and is movable in an axial direction. Once the tract dilator has been inserted until the distal tip 20 abuts the external wall of the blood vessel 102, as shown in FIG. 2, the depth indicator 30 is manually positioned adjacent the patient's skin 106. Alternatively, the depth indicator 30 can be pushed to a depth indicating position by the skin 106 as the dilator is inserted. Preferably, the depth indicator 30 is an elastic ring which is movable axially on the tract dilator 10 and maintains a measured position for comparison with the introducer 12.

A side view of an introducer 12 is illustrated in FIGS. 1 and 3. The introducer 12 includes a staging chamber 34 for receiving an absorbable sponge pledget 40 and a delivery chamber 36 for receipt of a hydrated and compressed pledget from the staging chamber. A tapered section 38 is provided between the staging chamber 34 having a larger diameter lumen and the delivery chamber 36 having a smaller diameter lumen. The tapered section 38 of the introducer 12 acts as a compression member to compress the hydrated pledget 40 into the delivery chamber. The introducer 12 also includes a luer fitting 42 at a proximal end for connection to a conventional syringe and wing members 44 for use in grasping the introducer.

The absorbable sponge pledget 40 according to one preferred embodiment of the invention is formed from a sheet of absorbable sponge material which has been cut into a rectangular shape and rolled to form a compact, substantially cylindrical, elongated pledget. The pledget 40 is sized to be received within the staging chamber 34 of the introducer 12 in a dry rolled state.

Once the pledget 40 has been inserted into the staging chamber 34 of the introducer 12, a conventional syringe 50 containing a hydrating fluid is connected to the luer fitting 42, as shown in FIG. 4. The pledget 40 is then hydrated within the staging chamber 34 by injecting a fluid into the staging chamber from the syringe 50 causing the pledget to swell, partially or fully blocking the lumen of the introducer. The partial hydration or wetting of the exterior surface of the pledget 40 creates a lubricous surface on the pledget. The hydrated pledget 40 is then forced into the delivery chamber 36 by injecting additional fluid with the syringe 50 to force the pledget through the tapered section 38 to the delivery chamber. For a somewhat smaller pledget 40, which does not entirely block the lumen of the introducer 12 after hydrating, the venture effect will help to draw the pledget into the delivery chamber 36. As shown in FIG. 5, a finger may be placed over the distal end of the introducer 12 during delivery of the pledget 40 to the delivery chamber 36 to prevent the pledget from being ejected from the introducer by the pressure of the fluid. Preferably, one or more vent holes 46 are provided in the side walls of the introducer adjacent the distal tip to allow air and liquid to escape from the introducer while the pledget 40 is positioned for delivery.

These vent holes 46 are small enough to prevent the pledget 40 from passing substantially into the vent holes.

As an alternative to placement of a finger at the distal end of the introducer 12 during advancement of the pledget 40 into the delivery chamber, a removable cap may be used. Further, the vent holes 46 may be omitted and a screen or a cap having a screen may be used to allow fluid to pass through the screen while the screen prevents the pledget 40 from being ejected.

The introducer 12 also includes a depth indicator 52 which is an axially movable member used to indicate the depth to which the introducer should be inserted into the patient to achieve the proper positioning of the pledget 40 at the puncture site. The depth indicator 52 of the introducer 12 is aligned with the depth indicator 30 on the tract dilator 10 to achieve proper pledget delivery positioning.

The introducer 12 may be formed in any known manner such as by injection molding from a plastic material. Preferably, the introducer 12 is transparent so that the pledget 40 can be viewed through the introducer and the user can visually confirm the pledget position. The introducer lumen may be provided with a reducing coating for improved pledget delivery. The delivery fluid also reduces friction for improved delivery by wetting the exterior surface of the pledget.

The pusher 14, as illustrated in FIG. 1, includes a distal end 56 which is configured to slide within the lumen of the delivery chamber 36 of the introducer 12. Preferably, there is a very small clearance or a resilient interference between the outer diameter at the distal end 56 of the pusher 14 and the inner diameter of the delivery chamber 36 to prevent portions of the pledget from getting caught between the pusher and the introducer 12. A resilient pusher distal end 56 or a sealing member on the pusher 14 may be used to accomplish or approach a resilient fit between the introducer 12 and the pusher.

The pusher 14 also may include a fitting 58 for connecting the proximal end of the pusher to the proximal end of the introducer 12. The fitting 58 acts as a stop to limit the motion of the pusher 14 with respect to the introducer 12. A female luer fitting 60 may also be included at the proximal end of the pusher 14 for connection of a syringe to the pusher for injection of beneficial agent through the pusher.

A method of delivering an absorbable sponge pledget 40 to facilitate hemostasis of a blood vessel puncture wound will now be described with respect to the steps illustrated in FIGS. 2–9. After an intravascular procedure has been completed, a guidewire 26 is already in place passing through the subcutaneous tissue into the blood vessel. Alternatively, if a guidewire is not already in place the guidewire is inserted through an access sheath used in the intravascular procedure and the access sheath is then removed. The guidewire 26 is maintained in place with a proximal end extending from the patient's body and a distal end extending through the skin 106 and subcutaneous tissue 104, through the blood vessel puncture 100, and into the blood vessel 102. As discussed above, the tract dilator 10 is threaded over the guidewire 26 and advanced down through the subcutaneous tissue 104 to an outside surface of the blood vessel 102. Resistance is felt when the tract dilator distal tip 20 contacts the exterior of the blood vessel and the tract dilator will not easily pass though the vessel puncture 100 and into the vessel. The depth indicator 30 on the tract dilator 10 is moved to abut the skin surface 106 indicating a distance from the skin surface to the blood vessel puncture site. The tract dilator 10 is then removed over the guidewire 26 and the introducer depth indicator 52 is aligned with the tract dilator depth indicator 30.

A sheet of absorbable sponge material is cut into a rectangle, is rolled tightly to form a pledget 40, and is placed into the staging chamber 34 of the introducer 12. The steps of cutting and rolling the pledget 40 and placing the dry pledget in the introducer staging chamber 34 may be performed before or after the intervascular procedure. Alternatively, the introducer 12 may be provided preloaded with a prepared pledget 40. With the pledget 40 placed in the introducer, the syringe 50 is filled with a hydrating fluid such as saline, thrombin, contrast agent, other therapeutic agent, or the like and attached to the introducer 12 as illustrated in FIG. 4. Fluid is injected slowly into the introducer 12 to hydrate the pledget 40. The user then pauses to allow hydration and initial swelling of the pledget 40. Sufficient hydration may occur in about 20 to 30 seconds or less depending on the size of the pledget 40.

As shown in FIG. 5, the user then places a finger over the distal end of the introducer 12 and injects fluid with the syringe 50 to force the pledget 40 through the tapered section 38 and into the smaller end or delivery chamber 36 of the introducer 12. Injection of fluid is stopped when the pledget 40 is positioned at the distal end of the delivery chamber 36. At this point the syringe 50 is removed and the introducer is loaded over the proximal end of the guidewire 26 for the delivery of the pledget 40 to the puncture site.

As shown in FIG. 6, a proximal end of the guidewire 26 is fed into the distal end of the introducer 12 though the hydrated and compressed pledget 40 and out the proximal end of the introducer. Preferably, the guidewire 26 is fed through substantially the center of the pledget 40 to insure that the implanted pledget is centered over the blood vessel puncture 100. Alternatively, the guidewire may be inserted along a side of the pledget 40, through a separate second lumen of the introducer, through an axial lumen in the pledget, or through a low density center of the pledget.

After feeding the guidewire 26 through the introducer, the guidewire 26 is fed through the pusher 14 and the pusher is advanced into the introducer until the distal end 56 of the pusher is in contact with the pledget 40. The introducer 12 and pusher 14 are then advanced together down though the skin 106 and the subcutaneous tissue 104 until the depth indicator 52 on the exterior of the introducer is at the skin level.

In the step illustrated in FIG. 7, the pusher 14 is held stationary while the introducer 12 is withdrawn proximally preferably to a distance of about 75% of the length of the compressed, hydrated pledget 40. This 75% withdrawal distance may be indicated with an appropriate marker on the introducer 12 or the plunger 14 or by contact between the fittings 42, 58 of the introducer and plunger. The portion of the pledget 40 ejected into the tissue quickly expands upon delivery to fill the available space and provide localized compression. With the pusher 14 and introducer 12 in the position illustrated in FIG. 7 and the pledget 40 partially ejected, a slight forward pressure is maintained by the operator on the introducer and pusher to increase local compression for a period of time of approximately 1 minute to allow hemostasis to begin. The forward pressure causes the pledget 40 to be compressed around the puncture site, as shown in FIG. 7. The guidewire 26 is then completely removed from the introducer 12 and the pusher 14. The introducer 12 is withdrawn the remaining approximately 25% by engaging the fitting 58 of the pusher with the female luer fitting 42 of the introducer to completely discharge the pledget 40 into the subcutaneous tissue 104 above the puncture site 100. A slight forward pressure can then be maintained by the operator on the introducer 12 and pusher 14 for approximately 1 minute before the introducer and pusher are removed from the tissue tract leaving the absorbable sponge pledget 40 positioned against the outer vessel wall, as shown in FIG. 9, providing local compression and facilitating hemostasis. The delivered pledget 40 maintains hemostasis until healing of the blood vessel 102 occurs. The pledget 40 is absorbed by the body over time.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 40 or may be cut with a punch or a stencil and knife and rolled to form a pledget as described above. Once hydrated, the pledget 40 can be easily compressed to fit into a lumen having a smaller cross sectional area than the original cross sectional area of the pledget. Additionally, the kneading of the hydrated pledget 40 during delivery encourages air trapped within the Gelfoam to be expelled and replaced with fluid, allowing rapid expansion upon delivery. When a pledget 40 of a pre-compressed Gelfoam is hydrated and kneaded (expelling air) during delivery, the pledget will have the absorption capacity to rapidly expand to many times (e.g., 3 or more times) its original dry volume upon delivery. When a pledget 40 of the non-compressed Gelfoam is hydrated and kneaded (expelling air) during delivery, the pledget will have the absorption capacity to rapidly expand to its original dry volume upon delivery. These properties make the Gelfoam sponge material particularly useful for facilitating hemostasis of puncture wounds by injection.

Abrupt lumen diameter changes within the introducer 12, such as at the tapered section 38, will improve "kneading" of the absorbable sponge material passing through the introducer. Manipulation of the dry absorbable sponge material, such as the rolling of the pledget 40, also provides kneading. Kneading improves hydration of the sponge material thereby improving the expansion properties of the hydrated delivered absorbable sponge.

According to alternative embodiments of the introducer, enlarged, recessed, or irregular areas in the lumen of the introducer are provided to impart additional kneading action to the absorbable sponge material further improving expansion properties of the sponge. FIG. 10 illustrates one such alternative embodiment of the introducer 12a in which the delivery chamber of the introducer is provided with two enlarged areas 64. As the absorbable sponge pledget 40 passes through the enlarged areas 64 of the introducer 12a, the material expands and is compressed by the introducer to increase kneading of the pledget. According to another alternative embodiment, the introducer may be provided with a plurality of staggered irregularities for improved kneading of the absorbable sponge pledget 40. The irregularities, enlargements, or recesses will preferably have a relatively smooth surface to prevent the absorbable sponge material from becoming caught as it passes through the introducer. Preferably, a length "l" between a distal end of the introducer 12 and the distal most of the irregularities, enlargements, or recesses is sufficient to accommodate the entire hydrated, compressed pledget such that the pledget 40 will not become trapped between the plunger and the enlargements.

Another alternative embodiment for improved kneading of the pledget 40 includes features on the guidewire, such as, irregularities, curves, bends, or the like. The guidewire kneading features will improve kneading of the pledget 40 as the guidewire 26 is inserted through the pledget.

The embodiment of FIG. 10 also includes a delivery chamber 36a provided with internal barbs 66 which help to retain the compressed pledget 40 positioned adjacent the distal end of the introducer 12a while the guidewire 26 is inserted through the pledget material. The internal barbs 66 are small enough to not cause interference with the passage of the pusher. In addition to or in place of internal barbs 66 other features may be used, such as ribs, a textured surface, holes, or the like.

The barbs 66 help to hold the pledget 40 in place as the guidewire 26 is inserted through the pledget. This is particularly useful when using a conventional coiled guidewire which creates a significant amount of friction when threaded through the absorbable sponge material. Alternatively, a plastic sheathed guidewire or hydrophilically coated guidewire can be used which is more easily threaded through the absorbable sponge material. A guidewire with a reduced diameter proximal portion will also facilitate threading of the guidewire 26 through the pledget 40.

As an alternative to the barbs 66 or a specially designed guidewire, the plunger 14 can be used to hold the pledget 40 in place during threading of the guidewire 26 through the pledget. A hydraulic back pressure can also be created to hold the pledget 40 in place by blocking the proximal end of the introducer 12, such as by the user's finger. Such a hydraulic back pressure will help to hold the pledget in place in the delivery chamber.

Although the use of a tract dilator 10 has been described above, the introducer 12 can be used in place of the dilator and the depth determining step can be performed while inserting the introducer, particularly where a plastic sheathed guidewire, other friction reducing guidewire, or other friction reducing feature is used.

FIG. 11 illustrates a cross section of a distal end of an introducer 12b according to an alternative embodiment of the invention in which a central lumen 70 is provided within the introducer for receiving the guidewire 26. The central lumen 70 allows the guidewire 26 to be inserted easily through the pledget 40. According to this embodiment the central lumen 70 is formed by a tube 72 which preferably extends at least the length of the hydrated pledget 40 when the pledget is positioned within the delivery chamber 36b. The tube 72 is supported by one or more ribs 74 connected to the exterior of the tube and to the interior wall of the introducer 12b. The pledget 40 for use with this embodiment is either formed with a generally U-shaped cross section to be accommodated in the U-shaped cross section of the delivery chamber 36b or deforms during loading to surround the one or more ribs 74 and tube 72.

FIG. 12 shows a proximal end of an introducer 12 connected to a specially designed connector 80 for connecting the introducer to the syringe 50. The connector 80 is used when the proximal end of the introducer 12 is larger in diameter than the standard syringe fitting. The connector 80 includes a first end 82 for connection to the syringe 50 and a second end 84 for connection to the introducer 12. In use, the connector 80 is removed from the adaptor 12. The pledget 40 is then inserted into the introducer 12 and the connector 80 is reattached. The syringe 50 is then connected to the connector 80 for injection of fluid into the introducer 12 to hydrate and compress the pledget 40.

Among other advantages this invention permits the delivery of more absorbable sponge material down a smaller tract by hydrating and compressing the absorbable sponge material. The over the wire delivery method ensures that the absorbable sponge pledget 40 is delivered directly over the puncture site and remains in the proper position while hemostasis is achieved. The vessel depth indicator system ensures that the absorbable sponge material is positioned adjacent the exterior of the blood vessel and does not extend into the blood vessel to possibly induce thrombosis. The kneading of the absorbable sponge material during rolling of the dry sponge and while hydrated and passing through the introducer improves the expansion properties of the sponge material.

The absorbable sponge material can be absorbed by the body in a period of time between several days and several months depending on the absorbable sponge material used. A pledget 40 formed of commercially available Gelfoam material will be absorbed by the body within 1 to 6 weeks. However, the pledget material may be engineered to provide different rates of absorption. For example, Gelfoam can be designed to be absorbed at different rates by varying the degree of cross-linking. Preferably, the pledget 40 is designed to be absorbed in less than one month.

Although the pledget 40 has been described as formed from a rectangular shaped piece of an absorbable sponge material which is rolled into a cylindrical shape, the pledget may also be formed in different shapes. For example, the pledget 40 may be preformed in a variety of cross sections including circular, rectangular, star, or other multi-sided shape. The pledget 40 may have a folded cross section and may have through or blind holes formed in the dry pledget. In addition, the pledget size and shape can be matched to the size and shape of a particular delivery site.

The continuous structure of the delivered absorbable sponge pledget 40 provides more secure and reliable placement of a plug of material against the blood vessel puncture than a paste or liquid. The continuous sponge structure can even facilitate partial withdrawal, removal, or movement of the ejected pledget. In accordance with one aspect of the invention, the absorbable sponge material can be hydrated with a clotting agent such as thrombin, a contrast agent, another beneficial agent, a combination of fluids, or the like.

The absorbable sponge pledget 40 may be presoaked with a beneficial agent such as thrombin for delivery of the beneficial agent to the punctured blood vessel. Alternatively, the pledget 40 may be hydrated with a beneficial liquid agent used as the hydrating fluid within the syringe 50. Further, the beneficial agent may be delivered to the pledget 40 after the pledget is ejected at the blood vessel puncture site through the lumen of the pusher 14 or through the introducer 12.

The treatment of a blood vessel puncture with a hydrated and injected pledget 40 of absorbable sponge to facilitate hemostasis provides substantial advantages in comfort over external pressure methods. In addition, the present invention also provides advantages over the insertion of a absorbable sponge material in a dry state or injection of a liquid or paste. In particular, the hydration and manipulation or "kneading" of the hydrated Gelfoam pledget 40 as it is passed through the introducer 12 improves the expansion and absorption characteristics of the Gelfoam. The injected Gelfoam conforms in shape quickly to the shape of the puncture site and immediately begins blocking blood flow through the puncture site and providing local compression. In contrast, a dry piece of sponge material does not swell until the blood has sufficiently saturated the sponge material, which can take up to hours. The hydrated and kneaded sponge material will expand to a larger size much more quickly when wetted than a piece of dry sponge material when wetted.

Because the amount of subcutaneous fat and tissue between the skin 106 and the blood vessel 102 varies between patients from approximately 0.5 cm to 15 cm or more the system may be provided in different lengths for use in different patients. The pledget 40 size and shape may also be varied for different patients. The absorbable sponge material should form a complete plug over the puncture site without expanding into the blood vessel or exiting the skin of the patient. In some instances where the amount of subcutaneous tissue is great it may be desirable to deliver multiple pledgets 40 in spaced apart positions along the tract leading to the puncture site.

The particular size and shape of the introducer 12 may vary depending on the size of the access site, amount of subcutaneous tissue, and the size of pledget 40 to be delivered. According to one example of the present invention, a pledget 40 is formed from a rectangular piece of pre-compressed Gelfoam approximately 2 by 3 cm with a thickness of 0.15 cm. The Gelfoam is rolled or folded into a pledget having a length of approximately 3 cm. An introducer 12 for delivery of this pledget to a patient with an average amount of subcutaneous tissue has a staging chamber length of about 2.5 to 6 cm, preferably approximately 3 cm, a staging chamber inner diameter of about 0.12 to 1.5 cm, preferably approximately 0.4 cm, and a delivery chamber 36 which is typically longer than the staging chamber and has an inner diameter smaller than that of the staging chamber of about 1 cm or less, preferably approximately 0.33 cm or less. The particular length of the delivery chamber 36 depends on both the subcutaneous tissue depth of the patient and the linear expansion of the pledget 40 as it moves from the staging chamber 34 to the delivery chamber. An angle made by a wall of the tapered section 38 with a longitudinal axis of the adaptor 12 may vary from about 5° to 90°, but is preferably between about 30° and 60°, more preferably approximately 45°. The tapered section 38 is illustrated with a substantially planar interior surface, when shown in cross section. However, the tapered section 38 may also have a convex or concave surface in cross-section. This example of pledget 40 and introducer 12 configurations is merely exemplary of the present invention.

In accordance with an alternative embodiment of the invention, the pledget 40 may be provided with a rapidly dissolvable tip extending from a distal end of the pledget. Examples of rapidly absorbable or dissolvable tip materials include water-soluble, biocompatible, non-toxic, and preferably non-immunogenic polymers such as poly vinyl alcohol (PVA) and ploy vinyl pyrrolidone (PVP). Other examples could include gelatin derived from porcine or bovine sources. Still other possible tip materials could include, but are not limited to, poly lactic-glycolic acid, poly (proline), ploy (ethylene oxide) and carbowaxes, methyl cellulose, carboxymethyl cellulose, poly (acrylic acid), poly (hydroxyethyl methacrylate), poly (acrylamide), natural plant gums, and poly (methyl vinyl ether-maleic anhydride). The rapidly dissolvable tip is arranged to extend slightly into the blood vessel and will provide an additional locating mechanism which will hold the pledget at the proper position over the puncture after the guidewire is removed in the step illustrated in FIG. 8. Preferably, the tip extends from the end of the pledget a length not shorter than one wall thickness of the target vessel and not exceeding one wall thickness plus the lumen diameter of the target vessel. Dissolution rates are sufficient to facilitate complete absorption of the rapidly dissolvable tip in the lumen within time periods as short as one minute and not exceeding 72 hours. Preferably, the pledget with the dissolvable tip can also be inserted without the use of the guidewire 26 and the dissolvable tip can serve the locating function of the guidewire for accurately positioning the pledget over the blood vessel puncture. The rapidly dissolvable tip may be formed from a thin walled tube which extends from an end of the pledget. For example, the thin walled tube may be rolled within the pledget. The guidewire may be threaded through the thin walled tube of the dissolvable locating tip or along one side the locating tip.

While the invention has been described in detail with reference to the preferred embodiments thereof, it will be apparent to one skilled in the art that various changes and modifications can be made and equivalents employed, without departing from the present invention.

What is claimed is:

1. A method for facilitating hemostasis of a puncture in the wall of a blood vessel, the method of comprising:
    establishing a depth of a blood vessel puncture of a patient;
    loading an introducer with a sponge pledget by hydrating and compressing the pledget, the introducer having a lumen including a staging chamber and a delivery chamber;
    loading the introducer over a guidewire positioned in the blood vessel by inserting the guidewire through the hydrated and compressed pledget; and
    ejecting the pledget adjacent the blood vessel puncture to facilitate hemostasis while maintaining the guidewire in place.

2. The method for facilitating hemostasis of a puncture in the wall of a blood vessel according to claim 1, wherein establishing a depth of a blood vessel is performed by introducing a tract dilator into a tissue tract until a distal end of the tract dilator abuts an exterior of the blood vessel wall.

3. The method for facilitating hemostasis of a puncture in the wall of a blood vessel according to claim 2, wherein a depth of the tract is indicated by a depth indicating member.

4. The method for facilitating hemostasis of a puncture in the wall of a blood vessel according to claim 1, wherein establishing a depth of a blood vessel is performed by introducing the introducer over the guidewire and into a tissue tract until a distal end of the introducer abuts an exterior wall of the blood vessel.

5. The method for facilitating hemostasis of a puncture in the wall of a blood vessel according to claim 1, wherein the pledget is partially ejected, compression is applied until hemostasis begins, and the pledget is then fully ejected.

6. The method for facilitating hemostasis of a puncture in the wall of a blood vessel according to claim 1, wherein the sponge pledget is rolled from a sheet of absorbable sponge prior to loading into the introducer.

7. The method for facilitating hemostasis of a puncture in the wall of a blood vessel according to claim 1, wherein loading the introducer includes injecting fluid into the introducer to hydrate and compress the pledget.

8. The method for facilitating hemostasis of a puncture in the wall of a blood vessel according to claim 7, wherein the introducer is provided with a distal vent for facilitating loading of the introducer.

9. A method for facilitating hemostasis of a puncture in the wall of a blood vessel, the method comprising:
    loading an introducer with a pledget of sponge;
    loading the introducer over a guidewire positioned in the blood vessel by inserting the guidewire through the loaded pledget;
    advancing the introducer with the loaded pledget through a tissue tract extending from a patient's skin to the puncture in the wall of the blood vessel without advancing the pledget relative to the introducer; and
    ejecting the pledget adjacent the puncture in the wall of the blood vessel to facilitate hemostasis.

10. The method for facilitating hemostasis of a puncture in the wall of a blood vessel according to claim 9, wherein loading the introducer involves hydrating and loading the pledget into the introducer.

11. The method for facilitating hemostasis of a puncture in the wall of a blood vessel according to claim 9, wherein loading the introducer involves compressing and loading the pledget into the introducer.

12. The method for facilitating hemostasis of a puncture in the wall of a blood vessel according to claim 9, wherein loading the introducer over the guidewire involves piercing the pledget with the guidewire.

13. The method for facilitating hemostasis of a puncture in the wall of a blood vessel according to claim 9, further comprising establishing a depth of the puncture in the wall of the blood vessel.

14. The method for facilitating hemostasis of a puncture in the wall of a blood vessel according to claim 13, wherein establishing a depth of a puncture is performed by introducing a tract dilator into a tissue tract until a distal end of the tract dilator abuts an exterior of the blood vessel wall.

15. The method for facilitating hemostasis of a puncture in the wall of a blood vessel according to claim 13, wherein establishing a depth of a puncture is performed by introducing the introducer over the guidewire and into a tissue until a distal end of the introducer abuts an exterior wall of the blood vessel.

16. The method for facilitating hemostasis of a puncture in the wall of a blood vessel according to claim 9, wherein the ejected pledget is positioned against an outer wall of the blood vessel.

17. The method for facilitating hemostasis of a puncture in the wall of a blood vessel according to claim 9, wherein the pledget expands upon delivery to fill the available space and provide localized compression.

18. The method for facilitating hemostasis of a puncture in the wall of a blood vessel according to claim 9, wherein the ejected pledget expands more quickly when wetted than a pledget of dry sponge material.

19. A method for advancing a pledget of sponge through the skin and subcutaneous tissue overlying a puncture in the wall of a blood vessel, the method comprising:
    loading an introducer with a pledget of sponge, the introducer having a lumen including a staging chamber and a delivery chamber;
    loading the introducer over a guidewire positioned in the blood vessel by inserting the guidewire through the loaded pledget; and
    advancing the introducer through the skin and subcutaneous tissue overlying the puncture in the wall of the blood vessel.

20. The method for advancing a pledget of sponge through the skin and subcutaneous tissue overlying a puncture in the wall of a blood vessel according to claim 19, wherein loading the introducer involves hydrating and loading the pledget into the introducer.

21. The method for advancing a pledget of sponge through the skin and subcutaneous tissue overlying a puncture in the wall of a blood vessel according to claim 19, wherein loading the introducer involves compressing and loading the pledget into the introducer.

22. The method for advancing a pledget of sponge through the skin and subcutaneous tissue overlying a puncture in the wall of a blood vessel according to claim 19, wherein loading the introducer over the guidewire involves piercing the pledget with the guidewire.

23. The method for advancing a pledget of sponge through the skin and subcutaneous tissue overlying a puncture in the wall of a blood vessel according to claim 19, further comprising establishing a depth of the puncture in the wall of the blood vessel.

24. The method for advancing a pledget of sponge through the skin and subcutaneous tissue overlying a puncture in the wall of a blood vessel according to claim 23, wherein establishing a depth of the puncture is performed by introducing a tract dilator into the subcutaneous tissue until a distal end of the tract dilator abuts an exterior of the blood vessel wall.

25. The method of advancing a pledget of sponge through the skin and subcutaneous tissue overlying a puncture in the wall of a blood vessel according to claim 23, wherein establishing a depth of the puncture is performed by introducing the introducer over the guidewire and into the subcutaneous tissue until a distal end of the introducer abuts an exterior wall of the blood vessel.

26. A method for facilitating hemostasis of a puncture in the wall of a blood vessel, the method comprising:
 loading an introducer with a pledget of a hemostasis material, wherein the loaded pledget is located in a distal end of the introducer;
 advancing the introducer with the loaded pledget through a tissue tract extending from a patient's skin to the puncture in the wall of the blood vessel without advancing the pledget relative to the introducer;
 locating an exterior of the blood vessel; and
 ejecting the pledget adjacent the exterior of the blood vessel.

27. The method for facilitating hemostasis of a puncture in the wall of a blood vessel according to claim 26, wherein the exterior of the blood vessel is located by tactile feedback upon contact with the exterior of the blood vessel.

28. The method for facilitating hemostasis of a puncture in the wall of a blood vessel according to claim 26, wherein the pledget of hemostasis material is absorbed within the body of the patient.

29. The method for facilitating hemostasis of a puncture in the wall of a blood vessel according to claim 26, further comprising loading the introducer over a guidewire by inserting the guidewire through the loaded pledget.

30. The method for facilitating hemostasis of a puncture in the wall of a blood vessel according to claim 26, wherein ejecting the pledget is performed by withdrawing the introducer.

31. A method for facilitating hemostasis of a puncture at an exterior surface of a blood vessel wall, comprising:
 advancing an introducer loaded with a pledget and a pusher through a tissue tract extending from a patient's skin to the exterior surface without advancing the pledget relative to the introducer and the pusher;
 holding the pusher stationary relative to the introducer at said exterior surface;
 withdrawing said introducer proximally to expose a distal end of the pledget; and
 applying a slight forward pressure on said pusher, whereby the pledget is simultaneously partially exposed and compressed against said exterior surface of the blood vessel puncture.

32. The method of claim 31 wherein said withdrawing comprises exposing approximately seventy-five percent (75%) of the pledget.

33. The method of claim 31 wherein said withdrawing comprises retreating said introducer to an identified marker on said introducer.

34. The method of claim 31 wherein said withdrawing further comprises:
 withdrawing a guidewire from said pusher and said introducer.

35. The method of claim 31 whereby said inserting further comprises mating a first fitting of said pusher with a second fitting of said introducer.

36. The method of claim 31 further comprising:
 maintaining a slight forward pressure on said pledget with said pusher; and
 withdrawing said introducer.

* * * * *

UNITED STATES PATENT AND TRADEMARK OFFICE
CERTIFICATE OF CORRECTION

PATENT NO. : 7,048,710 B1
APPLICATION NO. : 09/613439
DATED : March 23, 2006
INVENTOR(S) : Cragg et al.

It is certified that error appears in the above-identified patent and that said Letters Patent is hereby corrected as shown below:

On The Title Page (56) Other Publications:
Please remove:

"J P.M. Foran, et al , "Early Mobilisation After Percutaneous Cardiac Catheterisation Using Collagen Plug (VasoSeal) Haemostasis," Br Heart, vol 69 (1993) pp. 424-429.

Schrader, R., "Collagen Application," Catheterization and Cardiovascular Diagnosis, (1992) pp. 298-302.

JSR Gibbs, "Fermoral Arterial Hemostasis," Journal of Interventional Cardiology, v 5 (1992) pp. 85-88.

W.G. Kussmaul, "Rapid Arterial Hemostasis," Journal of the American College of Cardiology, vol. 25 (1995) pp. 1685-1692.

Timothy A. Sanborn, MD, et al , "Multicenter Randomized Trial Comparing a Percutaneous Collagen Hemostasis Device With Conventional Manual Compression After Diagnostic Angiography and Angioplasty," Journal of American College of Cardiology, vol. 22, No. 5 (1993) pp. 1273-1279"

And replace it with:

--J P M Foran, et al., "Early Mobilisation After Percutaneous Cardiac Catheterisation Using Collagen Plug (VasoSeal) Haemostasis," Br. Heart J., 69:424-429 (1993).

Schrader, R , et al "Collagen Application for sealing of Arterial Puncture Sites in Comparison to Pressure Dressing: A Randomized Trial," Catheterization and Cardiovascular Diagnosis, 27(4):298-302 (1992)

JSR Gibbs, "Femoral Arterial Hemostasis Using a Collagen Plug After Coronary Artery Stent Implantation," Journal of Interventional Cardiology, 5(2):85-88 (1992).

W.G. Kussmaul, "Rapid Arterial Hemostasis and Decreased Access Site Complications after Cardiac Catheterization and Angioplasty: Results of Randomized Trial of a Novel Hemostatic Device," Journal of the American College of Cardiology, 25(7):1685-1692 (1995).

UNITED STATES PATENT AND TRADEMARK OFFICE
CERTIFICATE OF CORRECTION

PATENT NO. : 7,048,710 B1
APPLICATION NO. : 09/613439
DATED : March 23, 2006
INVENTOR(S) : Cragg et al.

It is certified that error appears in the above-identified patent and that said Letters Patent is hereby corrected as shown below:

Timothy A. Sanborn, MD, et al., "Multicenter Randomized Trial Comparing a Percutaneous Collagen Hemostasis Device With Conventional Manual Compression After Diagnostic Angiography and Angioplasty," Journal of American College of Cardiology, 22(5): 1273-1279 (1993) --

On The Title Page (56)
On page 4, Column 2, under Other Publications:

Please remove:

"Turjman"

And replace it with:

--Turman --

Column 1, line 30, under Background of the Invention

Please remove:

"applied for a up to an hour or more during which time the"

And replace it with:

--applied for up to an hour or more during which time the --

Signed and Sealed this

Second Day of October, 2007

JON W. DUDAS
*Director of the United States Patent and Trademark Office*